(12) United States Patent
Regensburger et al.

(10) Patent No.: US 12,271,364 B2
(45) Date of Patent: Apr. 8, 2025

(54) SYSTEMS AND METHODS FOR REDUCTION OF PRIVACY RISK IN DATA

(71) Applicant: IMMUTA, INC., College Park, MD (US)

(72) Inventors: Joseph J. Regensburger, Grove City, OH (US); Alfred V. Rossi, III, Hilliard, OH (US); Sophie Stalla-Bourdillon, Florence (IT)

(73) Assignee: IMMUTA, INC., College Park, MD (US)

(*) Notice: Subject to any disclaimer, the term of this patent is extended or adjusted under 35 U.S.C. 154(b) by 389 days.

(21) Appl. No.: 17/592,714

(22) Filed: Feb. 4, 2022

(65) Prior Publication Data

US 2022/0253561 A1  Aug. 11, 2022

Related U.S. Application Data

(60) Provisional application No. 63/146,119, filed on Feb. 5, 2021.

(51) Int. Cl.
| | |
|---|---|
| *G06F 21/62* | (2013.01) |
| *A61K 31/519* | (2006.01) |
| *G06F 16/22* | (2019.01) |
| *G06F 16/242* | (2019.01) |
| *G06F 16/248* | (2019.01) |

(52) U.S. Cl.
CPC ........ *G06F 16/2282* (2019.01); *A61K 31/519* (2013.01); *G06F 16/243* (2019.01); *G06F 16/248* (2019.01); *G06F 21/6227* (2013.01); *G06F 21/6254* (2013.01)

(58) Field of Classification Search
None
See application file for complete search history.

(56) References Cited

U.S. PATENT DOCUMENTS

| | | | |
|---|---|---|---|
| 2009/0049069 A1* | 2/2009 | Aggarwal | H04L 63/0407 |
| 2015/0169895 A1* | 6/2015 | Gkoulalas-Divanis | G06F 21/6227 726/26 |
| 2016/0196453 A1* | 7/2016 | Yamaoka | G06F 21/6245 726/26 |
| 2018/0232488 A1* | 8/2018 | Jafer | G06F 21/6254 |
| 2019/0188402 A1* | 6/2019 | Wang | G06N 7/01 |
| 2020/0250315 A1* | 8/2020 | Sunkavally | G06F 21/6254 |
| 2020/0327252 A1* | 10/2020 | McFall | G06F 21/78 |
| 2021/0279219 A1* | 9/2021 | Fenton | G06F 16/221 |

* cited by examiner

*Primary Examiner* — Fatoumata Traore
(74) *Attorney, Agent, or Firm* — MH2 Technology Law Group, LLP (57) ABSTRACT

A method, system and computer program product are configured to access data, the data including a plurality of attributes, classify each of the attributes into one of a plurality of classifications, receive a privacy objective and a utility objective, determine a data transformation to achieve the privacy objective and the utility objective, apply the data transformation to the data, wherein the data transformation is applied to at least one of the attributes of the data based on the classifications to produce selectively modified data, iteratively refine data transformations through adjustment of utility objectives, and present the data for disclosure.

19 Claims, 7 Drawing Sheets

SYSTEMS AND METHODS FOR REDUCTION OF PRIVACY RISK IN DATA

CROSS-REFERENCE TO RELATED APPLICATIONS

This application claims the benefit of U.S. Provisional Patent Application No. 63/146,119 filed on Feb. 5, 2021, which is hereby incorporated by reference in its entirety.

FIELD OF THE DISCLOSURE

The techniques herein generally relate to data disclosure, and more particularly, but not exclusively, to systems and methods for reduction of privacy, such as the risk in re-identification in disclosure of data.

BACKGROUND

Many privacy-enhancing technologies (PETs) safe-guard individual's data through data modification or by moderating access to data elements with the goal of obtaining tolerable limits on some statistical measure of privacy, also known as a privacy objective.

As would be expected with statistical measures, it is often the case that there are many different possible modifications of the data which can satisfy formal privacy objectives. While there may be many ways to achieve privacy, not all are equally good from the point of view of (data) utility which considers the suitability of data for a given purpose.

Additionally, determining which of numerous PETs to use to implement one or more privacy objective and/or one or more utility objective can be difficult. Furthermore, implementing the selected PET can also be difficult, particularly for non-expert users.

SUMMARY

Disclosed herein are systems, methods, and computer program products for reduction of privacy risk in disclosure of data. In some embodiments, the data may be contained in a database and the systems may be used to reduce the privacy risk of data that is to be disclosed from the database.

In some embodiments, the systems and methods access data, the data including a plurality of attributes, classify each of the attributes into one of a plurality of classifications, receive a privacy objective and a utility objective, determine a data transformation to achieve the privacy objective and the utility objective, apply the data transformation to the data, wherein the data transformation is applied to at least one of the attributes of the data based on the classifications to produce selectively modified data, and present the data for disclosure.

In some embodiments, the systems and methods determine whether the privacy objective was met after applying the data transformation to the data. In some embodiments, the systems and methods determine whether a utility objective was met after applying the data transformation to the data.

BRIEF DESCRIPTION OF THE DRAWINGS

The accompanying drawings, which are incorporated into and constitute a part of this specification, illustrate implementations of the techniques herein and together with the description, serve to explain the principles of various embodiments.

DETAILED DESCRIPTION

Reference will now be made in detail to example implementations of the techniques herein, examples of which are illustrated in the accompanying drawings. Wherever convenient, the same reference numbers will be used throughout the drawing to refer to the same or like parts.

In accordance with embodiments described herein, a system, processes and computer-program products may be utilized to reduce privacy risk in data that is to be disclosed. As further described herein, the systems and methods are configured to access data, the data including a plurality of attributes, classify each of the attributes into one of a plurality of classifications, receive a privacy objective and a utility objective, determine a data transformation to utilize to achieve the privacy objective and the utility objective, apply the data transformation to the data, wherein the data transformation is applied to at least one of the attributes of the data based on the classifications to produce selectively modified data, and present the data for disclosure after application of the data transformation.

Unlike conventional systems, various embodiments of the systems and methods described herein instead apply one of a plurality of data transformations to data, to achieve one or more privacy objectives and one or more utility objectives, such as reducing the privacy risk of the data after disclosure. In accordance with various embodiments, by the system applying the data transformation, the administrators of the database do not have to understand how to apply the data transformation, which can be difficult. Moreover, such systems and methods can be used to augment the capabilities of databases which do not offer such features directly in product, including application of the data transformation to meet privacy requirements.

Embodiments may be utilized with disclosure of any type of data where privacy concerns are relevant. However, a particularly salient use case for embodiments occurs within the context of HIPAA Expert Determination of The HIPAA Privacy Rule enforced by the United States Department of Health and Human Services Office for Civil Rights (OCR).

The HIPAA Privacy Rule offers two methods for de-identifying Protected Health Information (PHI): the Expert Determination method (§ 164.514(b)(1)) and the Safe Harbor method (§ 164.514(b)(2)). While neither method ensures zero risk of re-identification when disclosing data, both facilitate the secondary use of data. The Safe Harbor method is often used because HIPAA defines it more precisely and it is thus easier to implement. The Expert Determination method, in contrast, offers more flexibility than the Safe Harbor method but relies upon the expert application of statistical or scientific principles that result in only a very small re-identification risk.

The HIPAA Privacy Rule (45 CFR § 164.514(b)) describes the Expert Determination method in the following way:

A person with appropriate knowledge of and experience with generally accepted statistical and scientific principles and methods for rendering information not individually identifiable:
 (i) Applying such principles and methods, determines that the risk is very small that the information could be used, alone or in combination with other reasonably available information, by an anticipated recipient to identify an individual who is a subject of the information; and
 (ii) Documents the methods and results of the analysis that justify such determination;

Narrowing risk to a "very small" one, under the Expert Determination method, can be a difficult task especially because the HIPAA Privacy Rule does not set any explicit numerical threshold. Best practice suggests that a "very small" risk should be based on widely accepted standards in the healthcare field, such as the threshold set forth by Centers for Medicare & Medicaid Services and state-of-the-art masking of direct identifiers and k-anonymization.

Requiring this process to be performed by a human is labor intensive and potentially unprincipled. Without clear and well-vetted standards for how the relevant privacy risk (in this case, re-identification risk) is measured and criteria under which this risk is deemed to be "very small", it is tedious and difficult to perform repeatable and reliable processes to satisfactorily reduce the relevant privacy risk. The system implementation described herein defines and automates the application of rules to achieve a very small privacy risk for a given set of data items and automatically generates a de-identified view of the data based on these rules, without creating duplicates.

In the context of HIPAA Expert Determination, the re-identification risks may be assessed using, e.g., the prosecutor attack model (Marsh et al., 1991; Dankar & El Emam, 2010). To elaborate on this example, under the prosecutor model it is assumed that a third party, known as the attacker, targeting a specific individual, wants to locate this individual's record within a dataset using publicly available information. To bound re-identification risk, this model makes a worst-case assumption that a potential attacker knows the complete set of public information about their target including information that, while theoretically is plausibly publicly knowable, may not be readily available. For instance, information that may only be reasonably obtained by (public) surveillance of the target. Using this information, the PET objective is to determine a data protection scheme that decreases the individual re-identification probability of all records (under, e.g., the prosecutor model), such that it is consistent with the "very small" threshold required by the HIPAA Privacy Rule.

In an example aiming to achieve objective privacy for HIPAA expert determination under the prosecutor model, an attacker is understood to re-identify an individual by matching attributes within a data source containing personal information, with aims to single out their target's data record. Attributes of the data which are beneficial to the attacker have the following properties ("Guidance on De-Identification of Protected Health Information" n.d.):

Replicability. An attribute is consistently associated with an individual. For example, such attributes include telephone number, name, or a congenital condition, whereas a highly variable attribute like body temperature may not be considered replicable.

Availability. An attribute is considered available if an individual's value can be discovered using reasonably-available public information such as telephone directories, social media, or voter registration rolls. For example, an address or gender is considered available, whereas a laboratory test may not be.

Distinguishability. An attribute is considered distinguishable if its value can be used to discriminate between individuals. For example, in a domestic context, a country would not be distinguishable whereas postal code would be.

Data privacy risk can be reduced by interfering with any one of these characteristics. To this end, data attributes may be categorized into four distinct groups by various embodiments:

Directly identifying attributes. Publicly known attributes that are uniquely associated with an individual. Being public, consistent, and unique, these attributes should be considered replicable, available, and distinguishable. These include but are not limited to medical record numbers, social security numbers, and full facial images.

Indirectly identifying attributes. Publicly known attributes that are not directly related to an individual but provide some discriminating power when attempting to identify an individual. Such attributes include but are not limited to postal code, gender, and age. In general, these attributes individually would be considered replicable and available, but not necessarily specific to an individual. However, when multiple indirect identifiers are combined, the resulting record could be highly specific.

Sensitive attributes. These are attributes which the subject does not want to be disclosed and are assumed to be not publicly known. Examples can include diagnosis, prescriptions, test results, etc. Since these attributes are not considered available, protecting them falls outside of the scope of reducing re-identification risk under the prosecutor model.

Insensitive attributes. These are attributes which are not publicly known but would not cause harm if released. This could include items like room temperature, traffic, or any other attribute which is neither sensitive nor could be associated with a subject.

In various embodiments, including embodiments related to HIPAA and embodiments unrelated to HIPAA, the relevant privacy risk, re-identification risk under the prosecutor model, can be reduced by applying various data rules or policies on the data which reduce either the replicability or distinguishability of attributes within the dataset. In practice this means applying rules to directly identifying attributes and indirectly identifying attributes (identifiers).

In various embodiments, including embodiments related to HIPAA and embodiments unrelated to HIPAA and unrelated to the prosecutor model, the values of directly identifying attributes (identifiers) may be replaced with NULL values to undermine the attributes' replicability.

More generally, in various embodiments, the distinguishability of records over indirectly identifying attributes may be reduced using a data transformation. The data transformation may utilize one or more PETs such as k-anonymization, randomized response, l-diversity, t-closeness, and other instance-specific data transformations arising as solver output from a constrained optimization problem involving the privacy objective and the utility objective, sufficient such that the privacy risk when the data is disclosed after application of the data transformation is sufficiently small under a specified privacy measure/objective. Each of these processes group subjects together into ambiguous groups, such that no one record can be distinguished from a predetermined threshold specifying a minimum number of individuals.

As an example, privacy risk under the prosecutor model is measured as the ratio of one over the size of the set of fewest number of mutually-indistinguishable individuals. In cases where an acceptable threshold is not codified, the minimum number of ambiguous individuals may be set using best practices or industry standards. As an example, the minimum group size as defined by the Centers for Medicare and Medicaid in the DUA (CMS-R-0235L) is 11, for a re-identification risk of (1/11 or about 9.09%).

Figure 1:
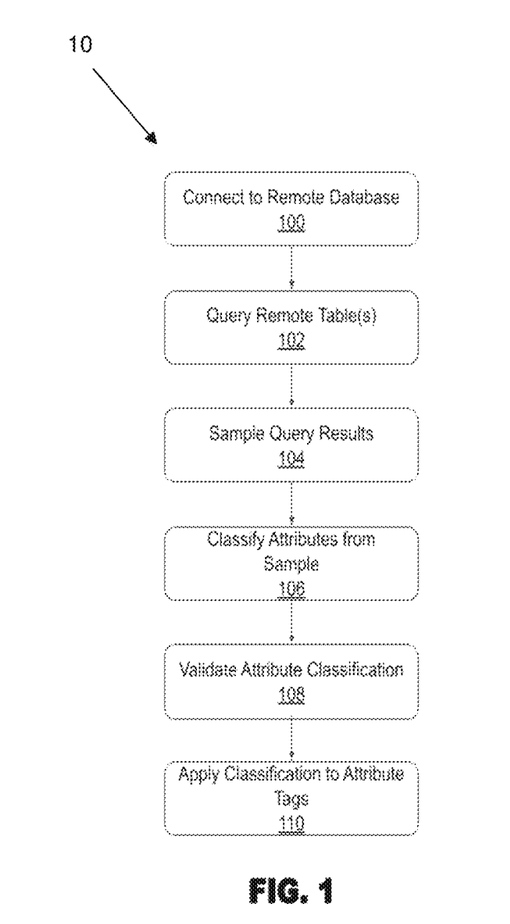
FIG. 1 is a flow chart illustrating an example of a method for registering data in a system prior to application of PETs, consistent with embodiments of the invention.

FIG. 1 is a flowchart illustrating an example of a method 10 that can be carried out by systems described herein for registering data in a system prior to application of one or more data transformations for reduction of privacy risk prior to disclosure of data, consistent with embodiments of the invention. As shown in FIG. 1, the method 90 begins with data, which may typically be stored in one or more remote databases, being connected to the systems described herein (block 100). Once connected, the remote database, which may be organized in table(s), is queried to create a virtualized table (block 102).

The data may be stored in a database, which in some embodiments may be a SQL database, stored in database objects called tables. A relation is a collection of related data entries and it consists of records and attributes. Relations are often depicted as tables, where attributes are organized into columns. For reasons of exposition, a relationship is sometimes conceptualized as a table, referring to records as "rows" and sequences of attribute values as "columns." A SQL database most often contains one or more tables. Each table may be identified by a name (e.g. "Customers" or "Orders"). The tables contain records (rows) with data. For example, consider the following dataset called Salaries:

TABLE 1

| ID | FirstName | LastName | Sex | Salary | Occupation |
|----|-----------|----------|-----|--------|------------|
| 1 | Jennifer | St John | F | $250,000 | Physician |
| 2 | Mark | McDowell | M | $ 57,400 | Teacher |
| 3 | Tina | Donaldson | F | $ 66,500 | Technician |
| 4 | Lisa | Smith | F | $ 48,000 | Technician |
| 5 | Tom | Robinson | M | $ 88,450 | Farmer |
| 6 | Brad | Stevens | M | $ 52,800 | Technician |

Table 1 includes 6 entries each having attributes of FirstName, LastName, Sex, Salary and Occupation. The methods disclosed herein may access data such as disclosed in Table 1 from the dataset to create the virtualized table.

The virtualized table may include a collection of attributes, which may be directly identifying, indirectly identifying, sensitive, and/or insensitive attributes. A sample (possibly without exclusion) of the data is selected from the virtualized table (block 104). This sample will contain representative elements of the query. Using the sample, the attributes are classified, for example as directly identifying attributes, indirectly identifying attributes, sensitive attributes, or insensitive (block 106) attributes as described herein. Various embodiments may use an algorithm or catalogue to perform classification of the attributes. In various embodiments, a skilled user may then validate the correctness of the classification of these attributes (block 108). Once validated, the attributes are tagged with the appropriate classification (block 110), which may be stored in the sample and/or the virtualized table. The classification of the attributes may later be utilized to determine which attributes to apply the PET(s) to.

Figure 2:
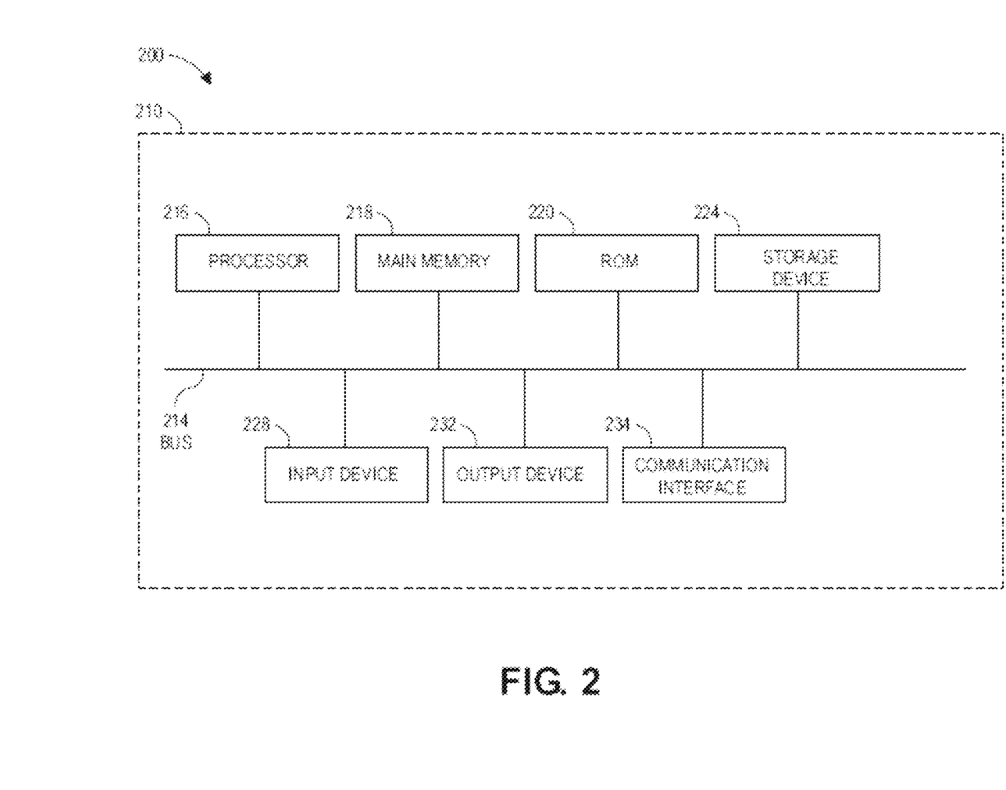
FIG. 2 is a block diagram of a computing system that may be used with embodiments described herein.

FIG. 2 shows a system block diagram illustrating an example of further details of the computing system of FIG. 1, illustrated as computing system 200, in accordance with aspects of the present disclosure. As shown in this example, the computing system 200 includes a computing device 210 capable of communicating via a network, such as the Internet. In example embodiments, the computing device 210 may correspond to a mobile communications device (e.g., a smart phone or a personal digital assistant (PDA)), a portable computer device (e.g., a laptop or a tablet computer), a desktop computing device, a server, etc. In some embodiments, the computing device 210 may host programming and/or an application to carry out the functions as described herein. The computing device 210 is configured to receive and/or obtain the datasets over communications interface 234, for example.

The computing device 210 may include a bus 214, a processor 216, a main memory 218, a read only memory (ROM) 220, a storage device 224, an input device 228, an output device 232, and a communication interface 234.

Bus 214 may include a path that permits communication among the components of device 210. Processor 216 may be or include a processor, a microprocessor, an application specific integrated circuit (ASIC), a field programmable gate array (FPGA), or another type of processor that interprets and executes instructions. Main memory 218 may include a random access memory (RAM) or another type of dynamic storage device that stores information or instructions for execution by processor 216. ROM 220 may include a ROM device or another type of static storage device that stores static information or instructions for use by processor 216. Storage device 224 may include a magnetic storage medium, such as a hard disk drive, or a removable memory, such as a flash memory.

Input device 228 may include a component that permits an operator to input information to device 210, such as a control button, a keyboard, a keypad, or another type of input device. Output device 232 may include a component that outputs information to the operator, such as a light emitting diode (LED), a display, or another type of output device. Communication interface 234 may include any transceiver-like component that enables device 210 to communicate with other devices or networks. In some implementations, communication interface 234 may include a wireless interface, a wired interface, or a combination of a wireless interface and a wired interface. In embodiments, communication interface 234 may receive computer readable program instructions from a network and may forward the computer readable program instructions for storage in a computer readable storage medium (e.g., storage device 224).

System 200 may perform certain operations, as described in detail below. System 200 may perform these operations in response to processor 216 executing software instructions contained in a computer-readable medium, such as main memory 218. A computer-readable medium may be defined as a non-transitory memory device and is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. A memory device may include memory space within a single physical storage device or memory space spread across multiple physical storage devices.

The software instructions may be read into main memory 218 from another computer-readable medium, such as storage device 224, or from another device via communication interface 234. The software instructions contained in main memory 218 may direct processor 216 to perform processes that will be described in greater detail herein. Alternatively, hardwired circuitry may be used in place of or in combination with software instructions to implement processes described herein. Thus, implementations described herein are not limited to any specific combination of hardware circuitry and software.

In some implementations, system 200 may include additional components, fewer components, different components, or differently arranged components than are shown in FIG. 2.

The system may be connected to a communications network (not shown), which may include one or more wired and/or wireless networks. For example, the network may include a cellular network (e.g., a second generation (2G) network, a third generation (3G) network, a fourth generation (4G) network, a fifth generation (2G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks. In embodiments, the communications network may include copper transmission cables, optical transmission fibers, wireless transmission, routers, firewalls, switches, gateway computers and/or edge servers.

The computing device 210 shown in FIG. 2 may be configured to receive or obtain a dataset or datasets and to reduce privacy risk in disclosure of the data as described herein. In some examples, the computing device 210 may be configured to obtain the dataset(s), apply data transformation(s) to attributes of the data, and send the data after application of the data transformation(s) to a user or other entity. In some examples, the data after application of the data transformations(s) produces a result with privacy and/or utility objectives being met.

One of ordinary skill will recognize that the components, arrangement, and implementation details of the computing system 210 are examples presented for conciseness and clarity of explanation. Other components, implementation details, and variations may be used, including adding, combining, or subtracting components and functions.

Figure 5:
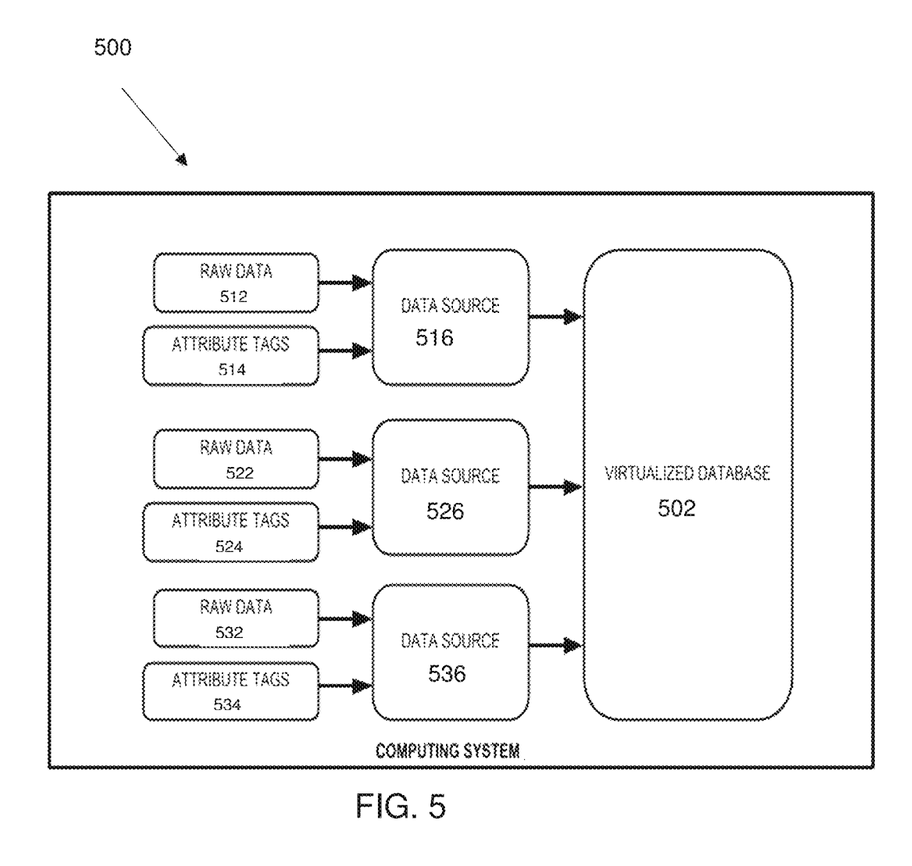
FIG. 5 is block diagram of a computing system that may be used with embodiments described herein.

FIG. 5 is a block diagram showing an example of a computing system 500 for organizing data within a virtual database 502, consistent with various embodiments. FIG. 5 demonstrates an example of how data is exposed within an accessible framework. In some embodiments, Multiple Data Sources (516, 526, and 536) are exposed within a Virtualized Database 502. Each of these data sources can include Raw Data (512, 532, and 522) and a set of attribute classifications (514, 524, and 534), among other things. The attribute classifications can be determined as described herein in conjunction with FIG. 1.

The example of FIG. 5 shows three notional data sources 516, 526, and 536, but this can be extended to an arbitrary number of data sources. The Raw Data (512, 522, 532) can be drawn from any relational database management system (RDBMS) or the like, including but not limited to Microsoft SQL Server, PostgreSQL, MySQL, Apache Impala, or Teradata. Various embodiments consistent with the invention may handle the data in its native format using SQL, for example, and do not interfere with the underlying data.

It is to be understood that the computing system or device 500 of FIG. 5 is for illustrative purposes only. In some embodiments, the computing device 500 can include additional software, sets of data, and the like.

Figure 3:
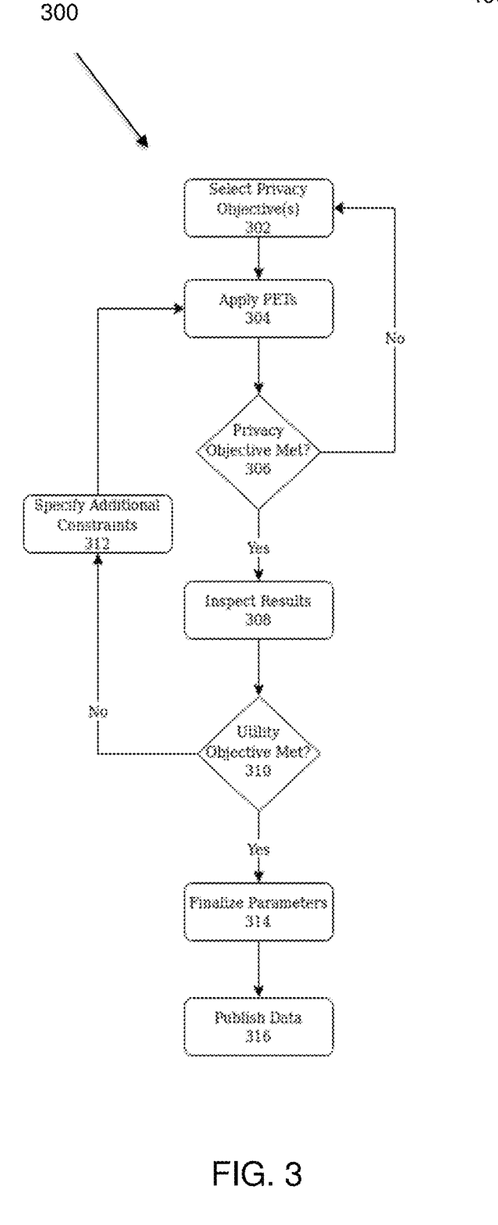
FIG. 3 is a flowchart of a process consistent with implementations described herein.

FIG. 3 illustrates an example of a generalized process or method 300 that may be carried out by systems described herein, under which a privacy objective is met, consistent with embodiments of the invention. FIG. 3 illustrates the application of policy rules onto the data. The process 300 begins by selecting one or more privacy objectives to apply (block 302). Examples of privacy-objectives may include, without limitation, 1) the re-identification risk does not exceed X % under the prosecutor model;
2) the re-identification risk does not exceed Y % under the journalist model;
3) the re-identification risk does not exceed Z % under the maximum knowledge intruder model;
4) that no Bayesian-optimal attacker may learn more than k-new bits of information about any individual;
5) that no Bayesian-optimal attacker may be able to use the data to significantly enhance their ability to guess a sensitive attribute; and
6) that no Bayesian-optimal attacker may be able to use the data to significantly enhance their guess as to whether or not information about a person of interest is included in the data.

In some embodiments, privacy objectives may be presented to a user for selection, and the systems and methods may then use the privacy objectives selected by the user. For example, the privacy objective could be presented to the user on a user interface for selection. In other embodiments, the privacy objectives may be selected by the system or preselected.

In order to achieve the desired privacy objectives, the system may apply one or more data transformation(s) to data before disclosure. Examples of such data transformations may be PETs such as k-anonymity, I-diversity, randomized response, and/or other PETs, and other instance-specific data transformations arising as solver output from a constrained optimization problem involving the privacy objective and the utility objective (block 304). The one or more data transformation(s) may be applied to the attributes of the data. In some embodiments, the one or more data transformation(s) are only applied to some of the attributes. For example, the data transformation(s) may only be applied to data attributes that have been classified as directly identifying attributes and/or indirectly identifying attributes, while not applying the data transformation(s) to attributes of the data that have been classified as sensitive attributes or insensitive attributes.

If necessary, the system continues to adjust internal data transformation parameters within (block 304) by automatic means until all objectives are simultaneously met, or the system proves that the given privacy objective(s) are not mutually obtainable, or it fails to find a solution within an acceptable number of steps or amount of time. Block 306, "Privacy Objective Met?", checks for failure of the previous step (Apply data transformations). In the event of failure, the user is returned to Select Privacy Objective(s) (block 302). Otherwise, the user is shown the results (Inspect Results, block 308). For example, the results may be presented to the user on a display. The user may be asked if the view of data after application of the data transformation(s) is acceptable for the use case (Utility Objective Met?, block 310). This step may involve automatic verification by measuring data utility and/or presenting sample data to a user for approval and/or additional input on further refinement. If utility is not met, the user may specify additional constraints, for example, such as specifying numeric weights encoding the user's tolerance for modification by attribute/column (block 312), as discussed herein in conjunction with FIG. 7.

If utility constraints have been added or modified, the system then resumes execution from Apply data transformations (block 304), by searching for a data transformation application that simultaneously satisfies privacy and the utility objectives implied by the specification of constraints. If the utility objective has not yet been met and the user wishes to continue then further parameter adjustment occurs, optionally with any additional information or under refined or alternative constraints provided by the user. If the utility objectives have been met then data transformation parameters are finalized and stored (block 314). Finally, in Publish Data (block 316) a policy encapsulating access to the data under application of the data transformations is provided with the finalized data transformation parameters. Published data may also be restricted to a set of allowed processing purposes with possibly different privacy and utility requirements. Therefore, the process of FIG. 3 may occur many times and result in different views of the same data possibly tailored to each allowed processing purpose.

FIG. 3 therefore illustrates an example of a process under which rules are generated for each use case and data with a low privacy risk or other met privacy objective is exposed for consumption, consistent with embodiments of the invention. In many circumstances, optimally satisfying the use case requires preferentially disclosing some attribute at the expense of redacting or otherwise obscuring one or more other attributes.

Figure 4:
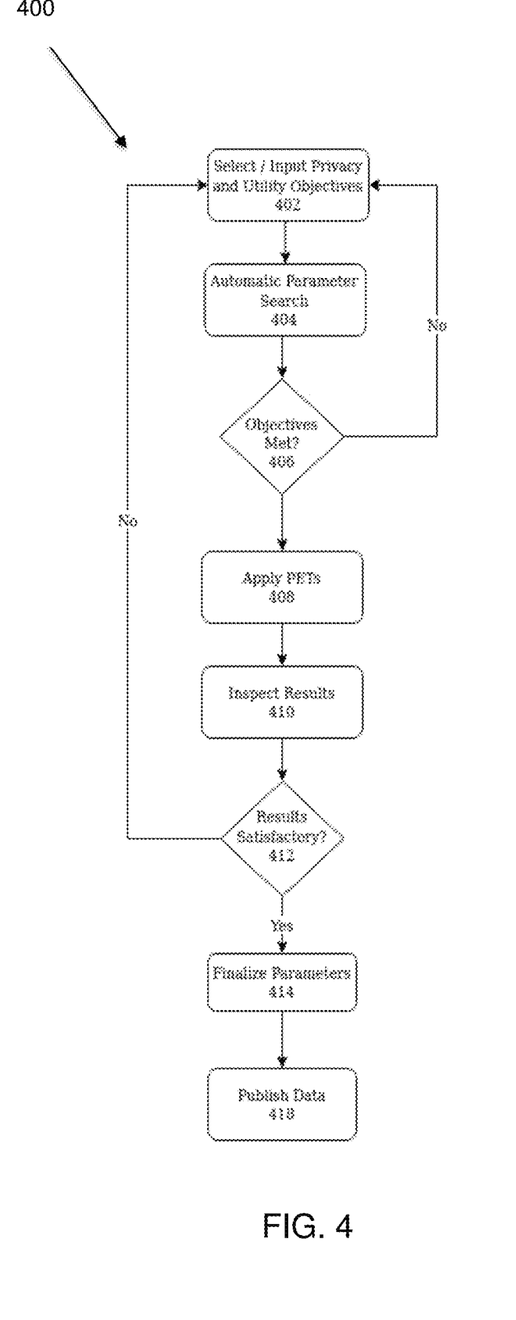
FIG. 4 is a flowchart of a process consistent with implementations described herein.

At a high level, the process 400 outlined in FIG. 4 is similar to the process 300 of FIG. 3, except that specification of utility objectives happen "up front" and are taken as constraints within the solver process in "Select/Input Privacy and Utility Objective(s)" (block 402). The user may input one or more privacy objectives and one or more utility objectives. In some embodiments, the user may be presented with a list or lists of objectives to choose from.

Examples of utility objectives may include, without limitation, 1) minimizing modification to declared fields of importance ("leave these fields alone");
2) preference for minimizing, to whatever extent possible, the number of value redactions occurring in specific attributes;
3) preference for minimizing, to whatever extent possible, the amount of modification (under various measures) of numerical values;
4) preference for preserving one, more, or possibly multiple key statistics, e.g. means, medians, modes, statistical variance; and
5) preferencing for minimizing expressions of the form $\Sigma_{i=1}^{N}|\mu(C_i)-\mu(P_\Theta(C_i))|^p$ where p>0, $\mu$ is a numeric measure, $P_\Theta$ denotes a PET achieving some privacy objective with parameters $\Theta$, and the sum is taken over a partition of records into cohorts $\{C_i\}_{i=1}^{N}$.

The system then searches for a set of parameters that result in the satisfaction of all constraints "Automatic Parameter Search" (block 404). Block 406, "Objectives Met?", checks for failure of the previous step (block 404). In the event of failure, the user is returned to Select/Input Privacy and Utility Objective(s) (block 402). Otherwise, the data transformation(s) are applied in the "Apply PETs" (block 408), and results are made available for inspection, perhaps via api, (Inspect Results, block 410). The results are evaluated for satisfaction (block 412). If they are not deemed satisfactory the process returns to "Select/Input Privacy and Utility Objective(s)" (block 402). Otherwise, parameters are finalized and stored (block 414). Finally, in Publish Data (block 418) a policy encapsulating access to the data under application of the data transformation(s) is provided with the finalized data transformation parameters. Published data may also be restricted to a set of allowed processing purposes with possibly different privacy and utility requirements. Therefore, the process of FIG. 4 may occur many times and result in different views of the same data possibly tailored to each allowed processing purpose.

Figure 6:
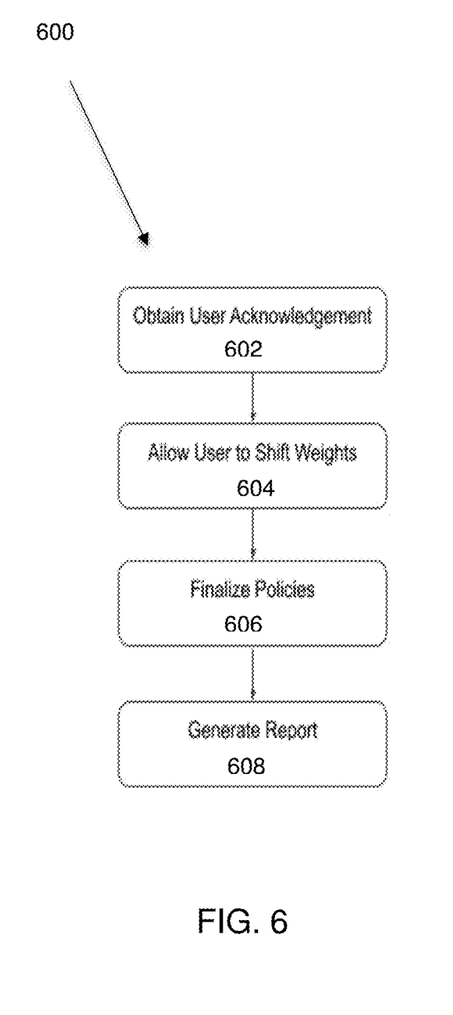
FIG. 6 is a flowchart of a process consistent with implementations described herein

The process 600 of preferentially disclosing some attributes to best satisfy a specific analytical use case is shown in FIG. 6. This process 600 is a special case of utility optimization and a specific feature of some embodiments of the invention. This process 600 allows a user to optimize the utility of the anonymization process to best satisfy the relevant analytical use case. To achieve this or other relevant privacy or utility customization, a user may desire to limit processing to some predefined purpose (block 602), especially in cases where the analytical use case requires higher fidelity access to more sensitive data elements. Once access is granted, a user may further modify privacy parameters to preferentially disclose higher fidelity information for the end use case of interest to the user (block 604) by modifying a weight(s) or other parameters associated with the PETs. Once these weights and/or other data transformation parameters are finalized (block 606), an automated report will be generated (block 608). In various embodiments, a report may contain the results of the statistical analysis for privacy and utility, as well as information about relevant laws, regulations, and anonymization rules pertinent to the use case. In some embodiments, this report may serve to document relevant findings regarding governed use of the data and may serve to document the compliance thereunder. In some embodiments, this report may be suitable for adoption as a determination report on behalf of or by an expert as under, e.g., HIPAA expert determination (45 CFR § 164.514 b1).

Figure 7:
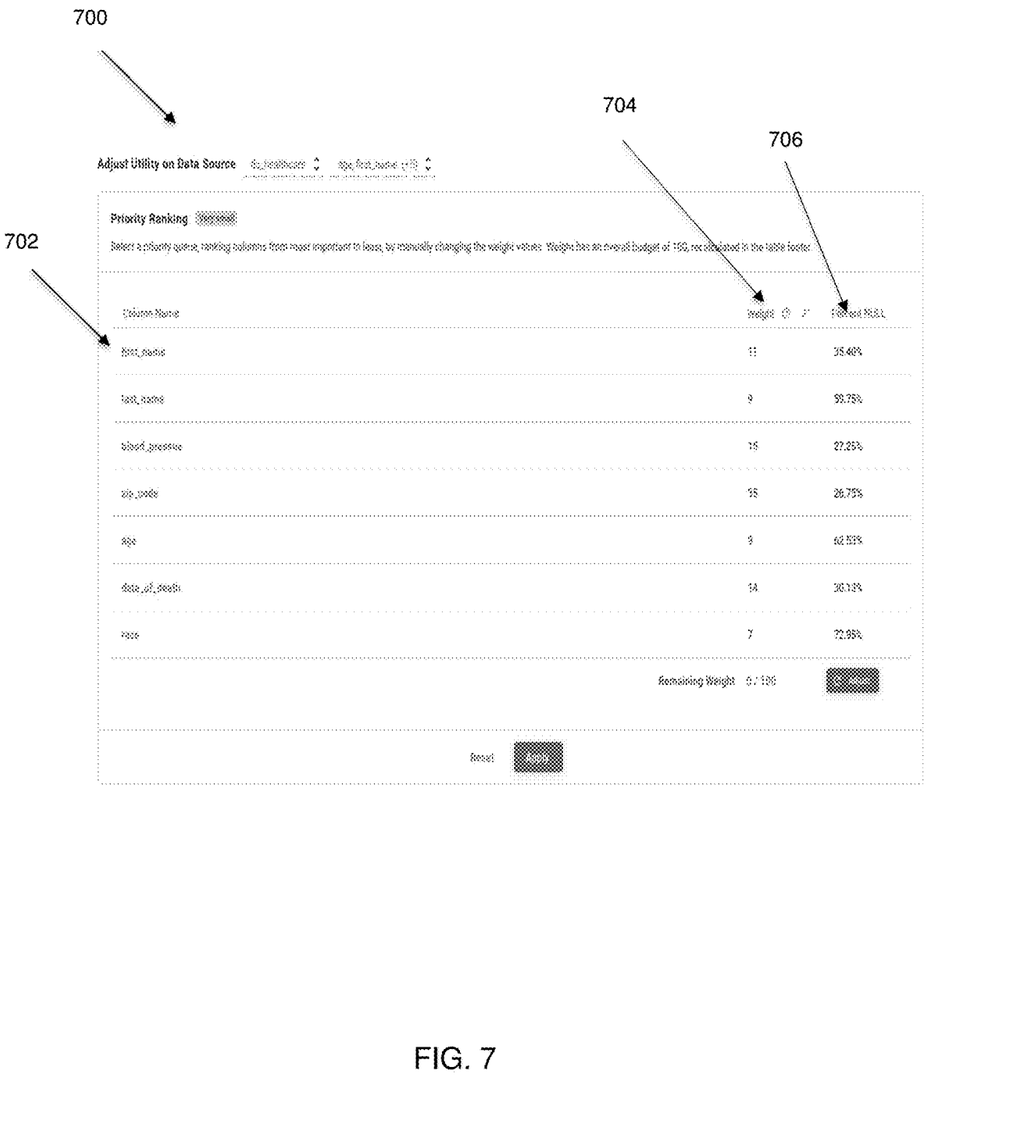
FIG. 7 is a graphical user interface that may be used with embodiments described herein.

FIG. 7 is an example user interface 700 that may be presented to a user for selection of weights that may be applied to attributes during application of PETs. The user interface 600 present attributes 702, which in this example include attributes of first_name, last_name, blood_pressure, zip_code, age, date_of_death and race, although any attributes may be used with datasets.

The user interface 700 further includes a weight column 704, which allows a user to adjust a weight 704 to be applied to each attribute. The weight 704 can be used to adjust application of the PET(s) to each attribute. The user interface 700 may also include a null column 706, which may change with changing of the weight 604, and indicate a percentage of how often a null value will be entered by the PET(s) in place of the original attribute value, for example.

Figure 8:
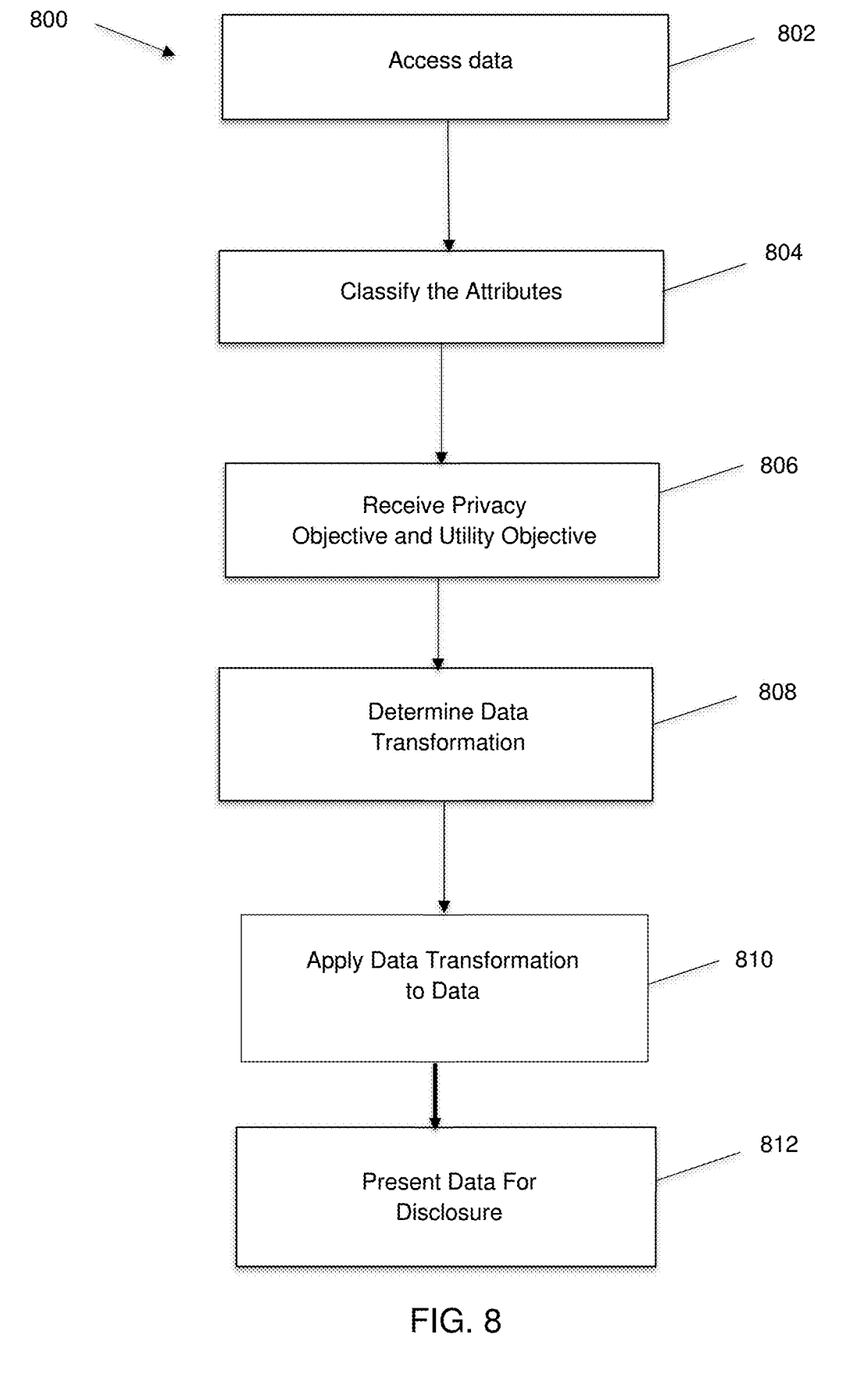
FIG. 8 is a flowchart of a process consistent with one or more implementations described herein.

FIG. 8 is an example process flow diagram of a method 800 for reduction of privacy risk in disclosure of data. In some embodiments, the method 800 can be implemented with any suitable computing device such as computing system 200 of FIG. 2, or computing system 500 of FIG. 5, among others.

At block 802, the method 800 accesses the data, the data including a plurality of attributes. The data may be accessed by any known methods, such as over an Internet connection, a LAN connection, a disc, etc.

At block 804, the method 800 classifies each of the attributes of the data into one of a plurality of classifications. In some embodiments, the classifications may include directly identifying attributes, indirectly identifying attributes, sensitive attributes and insensitive attributes.

At block 806, the method 800 receives a privacy objective and a utility objective. In some embodiments, privacy objectives may be presented to the user for selection, such as by presenting the privacy objectives on a user interface.

At block 808, the method 800 determines a data transformation such as a privacy enhancing technology to utilize to achieve the selected privacy objective.

At block 810, the method 800 applies the data transformation to the data. The data transformation is applied to selected ones of the attributes of the data based on the classifications of the attributes to selectively modify the data.

At block 812, the method 800 presents the data for disclosure after application of the data transformation. In some embodiments, the data may be presented on a user interface.

It should be noted that the term "approximately" or "substantially" may be used herein and may be interpreted as "as nearly as practicable," "within technical limitations," and the like. In addition, the use of the term "or" indicates an inclusive or (e.g., and/or) unless otherwise specified.

Other implementations of the techniques herein will be apparent to those skilled in the art from consideration of the specification and practice of the embodiments disclosed herein. It is intended that the specification and various embodiments be considered as examples only.

What is claimed is:

1. A computer-implemented method for reducing privacy risk in a disclosure of data, the method comprising:
    accessing, by a computing device, the data, the data including a plurality of attributes;
    classifying, by the computing device, each attribute among the plurality of attributes into one of a plurality of classifications;
    presenting a plurality of privacy objectives to a user;
    receiving, by the computing device, a selection of one of the privacy objectives from the user;
    receiving a selection of a utility objective;
    determining, by the computing device, a data transformation to achieve the selected privacy objective and the selected utility objective, wherein the data transformation comprises at least one of: k-anonymization, randomized response, I-diversity, t-closeness or other instance-specific data transformations arising as solver output from a constrained optimization problem involving the privacy objective and the utility objective;
    applying, by the computing device, the determined data transformation to the data, wherein the determined data transformation is applied to at least one of the attributes of the data based on the classifications to produce selectively modified data;
    determining, by the computing device, whether the selected privacy objective and the selected utility objective have been met after application of the determined data transformation to the data;
    iteratively adjusting and re-applying the data transformation to the data, by the computing device, if the selected utility objective is determined to not have been met; and
    presenting, by the computing device, the selectively modified data for disclosure.

2. The computer-implemented method of claim 1, wherein the plurality of classifications include directly identifying attributes, indirectly identifying attributes, sensitive attributes and insensitive attributes.

3. The computer-implemented method of claim 2, wherein applying, by the computing device, the determined data transformation to the data comprises: applying the determined data transformation to the directly identifying attributes of the data.

4. The computer-implemented method of claim 2, wherein applying, by the computing device, the determined data transformation to the data comprises:
    applying the determined data transformation to the direct attributes of the data and not applying the privacy enhancing technology to the sensitive attributes and the insensitive attributes of the data.

5. The computer-implemented method of claim 1, further comprising receiving an attribute weighting value from the user, the attribute weighting value indicating a weighting for at least one of the plurality of attributes, wherein the attribute weighting value varies the applying of the data transformation to the at least one of the attributes.

6. The computer-implemented method of claim 5, further comprising presenting a user interface to the user, the user interface including a plurality of attribute weighting values from which the user can select.

7. The computer-implemented method of claim 1, further comprising selecting a different privacy objective if the selected privacy objective and/or the utility objective have not been met.

8. A system for reducing of privacy risk in a disclosure of data, the system comprising:
    one or more processors; and
    a memory coupled to the one or more processors, the memory storing instructions, which when executed by the one or more processors, cause the one or more processors to perform operations comprising:
    accessing the data, the data including a plurality of attributes;
    classifying each attribute among the plurality of attributes into one of a plurality of classifications;
    presenting a plurality of privacy objectives to a user;
    receiving a selection of one of the privacy objectives from the user;
    receiving a selection of a utility objective;
    determining a data transformation to achieve the selected privacy objective and the selected utility objective, wherein the data transformation comprises at least one of: k-anonymization, randomized response, I-diversity, t-closeness or other instance-specific data transformations arising as solver output from a constrained optimization problem involving the privacy objective and the utility objective;
    applying the determined data transformation to the data, wherein the determined data transformation is applied to at least one of the attributes of the data based on the classifications to produce selectively modified data;

iteratively adjusting and re-applying the data transformation to the data, by the computing device, if the selected utility objective is determined to not have been met; and presenting the selectively modified data for disclosure.

9. The system of claim 8, wherein the plurality of classifications include directly identifying attributes, indirectly identifying attributes, sensitive attributes and insensitive attributes.

10. The system of claim 9, wherein the operations further comprise applying the determined data transformation to the directly identifying attributes of the data.

11. The system of claim 10, wherein the operations further comprise applying the determined data transformation to the directly identifying attributes of the data and not applying the data transformation to the sensitive attributes of the data and to the insensitive attributes of the data.

12. The system of claim 10, wherein the operations further comprise selecting a different privacy objective if the selected privacy objective has not been met.

13. The system of claim 8, wherein the operations further comprise:
presenting a user interface to the user, the user interface including a plurality of attribute weighting values from which the user can select; and
receiving an attribute weighting value selected by the user through the user interface, wherein the attribute weighting value indicates a weighting for at least one of the plurality of attributes, and the attribute weighting value varies the applying of the data transformation to the at least one of the plurality of attributes.

14. A non-transitory computer-readable medium storing instructions which, when executed by one or more processors of a system, cause the system to reduce risk in a disclosure of data by performing operations comprising:
accessing, by a computing device, the data, the data including a plurality of attributes;
classifying, by the computing device, each attribute among the plurality of attributes into one of a plurality of classifications;
presenting a plurality of privacy objectives to a user;
receiving, by the computing device, a selection of one of the privacy objectives from the user;
receiving, by the computing device, a selection of a utility objective;
determining, by the computing device, a data transformation to achieve the selected privacy objective and the selected utility objective, wherein the data transformation comprises at least one of: k-anonymization, randomized response, I-diversity, t-closeness or other instance-specific data transformations arising as solver output from a constrained optimization problem involving the privacy objective and the utility objective;
applying, by the computing device, the determined data transformation to the data, wherein the determined data transformation is applied to at least one of the attributes of the data based on the classifications to produce selectively modified data;
iteratively adjusting and re-applying the data transformation to the data, by the computing device, if the selected utility objective is determined to not have been met; and
presenting the selectively modified data for disclosure.

15. The non-transitory computer-readable medium of claim 14, wherein the plurality of classifications include directly identifying attributes, indirectly identifying attributes, sensitive attributes and insensitive attributes.

16. The non-transitory computer-readable medium of claim 15, wherein applying, by the computing device, the determined data transformation comprises applying the determined data transformation to the directly identifying attributes of the data.

17. The non-transitory computer-readable medium of claim 16, wherein applying, by the computing device, the determined data transformation comprises applying the determined data transformation to the directly identifying attributes of the data and not applying the determined data transformation to the sensitive attributes of the data and to the insensitive attributes of the data.

18. The computer-implemented method non-transitory computer-readable medium of claim 14, further comprising selecting a different privacy objective if the selected privacy objective has not been met.

19. The computer-implemented method non-transitory computer-readable medium of claim 14, further comprising:
presenting a user interface to the user, the user interface including a plurality of attribute weighting values from which the user can select; and
receiving an attribute weighting value selected by the user through the user interface, wherein the attribute weighting value indicates a weighting for at least one of the plurality of attributes, and the attribute weighting value varies the applying of the data transformation to the at least one of the plurality of attributes.

\* \* \* \* \*